US012797232B2

(12) United States Patent
Czaplewski et al.

(10) Patent No.: US 12,797,232 B2
(45) Date of Patent: Nov. 17, 2026

(54) OSTOMY POUCH INCLUDING MULTI-STAGE FILTER PROTECTION

(71) Applicant: Hollister Incorporated, Libertyville, IL (US)

(72) Inventors: Gregory J. Czaplewski, Bloomingdale, IL (US); Kanav Kumar, Chicago, IL (US)

(73) Assignee: HOLLISTER INCORPORATED, Libertyville, IL (US)

(*) Notice: Subject to any disclaimer, the term of this patent is extended or adjusted under 35 U.S.C. 154(b) by 401 days.

(21) Appl. No.: 17/801,943

(22) PCT Filed: Mar. 18, 2021

(86) PCT No.: PCT/IB2021/000228
§ 371 (c)(1),
(2) Date: Aug. 24, 2022

(87) PCT Pub. No.: WO2021/186249
PCT Pub. Date: Sep. 23, 2021

(65) Prior Publication Data
US 2023/0099447 A1 Mar. 30, 2023

Related U.S. Application Data

(60) Provisional application No. 62/992,648, filed on Mar. 20, 2020.

(51) Int. Cl.
*A61F 5/441* (2006.01)
*A61F 5/445* (2006.01)

(52) U.S. Cl.
CPC .............. *A61F 5/441* (2013.01); *A61F 5/445* (2013.01)

(58) Field of Classification Search
CPC ........................... A61F 5/441; A61F 5/44–445
See application file for complete search history.

(56) References Cited

U.S. PATENT DOCUMENTS 4,668,258 A * 5/1987 Steer ..................... B32B 27/065 96/135
4,778,601 A * 10/1988 Lopatin .............. B01D 67/0095 210/500.36

(Continued)

FOREIGN PATENT DOCUMENTS

CN 1251980 A 5/2000
CN 1551750 A 12/2004

(Continued)

OTHER PUBLICATIONS

Blue Thunder Technologies. An Introduction into SMS Material. Blue Thunder Technologies, May 23, 2019, [online], [retrieved on Nov. 15, 2024]. Retrieved from the Internet: <URL: https://bluethundertechnologies.com/introduction-sms-material/> (Year: 2019).*

(Continued)

*Primary Examiner* — Leslie R Deak
*Assistant Examiner* — Linnae E. Raymond
(74) *Attorney, Agent, or Firm* — Klintworth & Rozenblat LLP

(57) ABSTRACT

An ostomy pouch includes a filter assembly and a multi-stage filter protection. The filter assembly includes a membrane layer, a backing layer, and a filter media arranged therebetween. The filter assembly is attached to one of the pouch walls such that the membrane layer covers a gas outlet. The multi-stage filter protection may include a prefilter formed from a foam and a microperforated protective panel covering the prefilter.

18 Claims, 12 Drawing Sheets

(56) References Cited

U.S. PATENT DOCUMENTS

| | | | | | |
|---|---|---|---|---|---|
| 5,074,851 | A * | 12/1991 | Plass | A61F 5/441 | 55/385.4 |
| 5,250,042 | A * | 10/1993 | Torgalkar | A61F 5/441 | 604/339 |
| 5,306,264 | A * | 4/1994 | Ferguson | A61F 5/441 | 604/338 |
| 5,401,264 | A * | 3/1995 | Leise, Jr. | A61F 5/441 | 604/333 |
| 5,643,234 | A * | 7/1997 | Lesko | A61F 5/441 | 604/338 |
| 5,672,163 | A * | 9/1997 | Ferreira | A61F 5/441 | 604/333 |
| 6,135,986 | A | 10/2000 | Leisner et al. | | |
| 6,506,184 | B1 * | 1/2003 | Villefrance | A61F 5/441 | 604/333 |
| 2005/0070863 | A1 | 3/2005 | Bulow et al. | | |
| 2006/0271002 | A1 * | 11/2006 | Botten | A61F 5/441 | 604/339 |

FOREIGN PATENT DOCUMENTS

| | | | | |
|---|---|---|---|---|
| CN | 107243185 | A * | 10/2017 | B32B 5/26 |
| JP | H06-277245 | A | 10/1994 | |
| JP | H10-033580 | A | 2/1998 | |
| JP | 2017-513617 | A | 6/2017 | |
| WO | WO-2006048019 | A1 * | 5/2006 | A61F 5/441 |
| WO | WO-2009080041 | A1 * | 7/2009 | A61F 5/441 |
| WO | WO-2013102009 | A1 * | 7/2013 | A61F 5/4404 |
| WO | WO-2015110544 | A1 * | 7/2015 | A61F 5/441 |

OTHER PUBLICATIONS

Written Opinion issued by ISA/EPO in connection with PCT/IB2021/000228 on Aug. 18, 2021.

International Search Report issued by ISA/EPO in connection with PCT/IB2021/000228 on Aug. 18, 2021.

International Preliminary Report on Patentability issued by ISA/EPO in connection with PCT/IB2021/000228 on Sep. 20, 2022.

European Search Report issued in connection with EP patent application No. EP20230211546 dated Apr. 25, 2024, 7 Pages.

Japanese Office Action issued in connection with JP application No. JP2022-555925 dated May 20, 2025, 04 pages.

European Office Action issued in connection with application No. 23211546.9 dated Mar. 9, 2026, 05 pages.

Australian Office Action issued in connection with application No. 2021236958 dated Dec. 18, 2025, 04 pages.

Australian Office Action issued in connection with application No. 2021236958 dated Mar. 16, 2026, 04 pages.

* cited by examiner

OSTOMY POUCH INCLUDING MULTI-STAGE FILTER PROTECTION

This is a National Stage Application of International Patent Application No. PCT/IB2021/000228 filed Mar. 18, 2021, which claims the benefit of and priority to U.S. Provisional Application No. 62/992,648 filed Mar. 20, 2020, the entirety of which are incorporated fully herein by reference.

BACKGROUND

The following description relates to an ostomy appliance, and more particularly, an ostomy pouch including a deodorizing filter and a multi-stage filter protection.

An ostomy bag or pouch includes an inlet configured to receive liquid, semisolid or solid bodily waste discharged from a stoma for collection within the pouch. A known pouch also includes a filter assembly to facilitate odor filtering and egress of gas from the pouch. However, in some instances, liquid, semisolid or solid contents (i.e., bodily waste) may flow to and block the filter assembly, thereby restricting egress of gas through the filter assembly. This may lead to ballooning of the pouch caused by a build-up of gas pressure and undesirable inflation of the pouch.

Disruption to quality of life from the pouch ballooning can be significant for ostomates, for example, anxiety, lack of discretion, fear of leakage, night time considerations, inconvenient user intervention to release gas pressure, etc. Some common methods to release built-up gas include opening a pouch coupling system, which is often referred to as "burping", draining a pouch, and peeling back a skin barrier. Many ostomates have reported spending many hours troubleshooting the pouch ballooning issues and feeling resigned about the current ostomy pouch systems.

Accordingly, it is desirable to provide an improved ostomy pouch system that can minimize ballooning while still providing comparable or better odor filtration.

SUMMARY

In one aspect, an ostomy pouch including a filter assembly and a multi-stage filter protection is provided. The ostomy pouch may include a body-side wall and a distal-side wall joined at an outer periphery and defining an interior volume comprising a collection area. The ostomy pouch may further comprise an inlet for receiving ostomy effluent and an outlet for egress of gas collected in the collection area. The filter assembly may be arranged to cover the outlet. The multi-stage filter protection may be configured to protect the filter assembly and may comprises a prefilter and a protective panel covering the prefilter.

In an embodiment, the filter assembly may be attached to an outer surface of one of the body-side wall and the distal-side wall, and the multi-stage protection may be arranged inside the pouch. For example, the filter assembly may be attached to an outer surface of the distal-side wall and the prefilter and the protective panel may be attached to an inner surface of the distal-side wall. In other embodiments, the filter assembly and the multi-stage protection may be arranged inside the pouch.

The protective panel may be formed from a microperforated film, an embossed film, or a microperforated embossed film. In an embodiment, the protective panel may be formed from a microperforated film comprising a plurality of openings having a diameter of about 100 μm to 500 μm, wherein the plurality of openings may be arranged to provide a pore-density of about 25 ppi to about 300 ppi. The protective panel may be sealed to the distal-side wall and/or to the body-side wall along an outer peripheral seal. The plurality of openings may be provided in a portion of the protective panel or throughout the entire surface of the protective panel. For example, the plurality of openings may be provided in a lower portion or an upper portion of the protective panel.

In an embodiment, the protective panel may be formed from a microperforated film including a first set of microperforations comprising a plurality of openings having a diameter of about 300 μm to about 500 μm and a second set of microperforations comprising a plurality of openings having a diameter of about 50 μm to about 200 μm, wherein the first set of microperforations may be arranged proximate a lower periphery of the protective panel and the second set of microperforations may be arranged above the first set of microperforations. In such an embodiment, the first set of microperforations may be configured to allow ostomy effluent accumulated between the protective panel and the pouch wall to flow down to the collection area. The second set of microperforations may be provided in at least about 30% of the protective panel area at a pore-density of about 100 ppi to about 200 ppi to allow gas to flow through the protective panel even after some of the microperforations are blocked by ostomy effluent.

The protective panel may be sealed to the distal-side wall along a lower periphery to provide a horizontal seal. A portion of the protective panel proximate the filter assembly may be free of microperforations. The horizontal seal may be a discontinuous heat seal or the protective panel may include at least one slit or opening proximate the lower periphery configured to allow liquid accumulated between the protective panel and the distal-side wall to flow down into the collection area.

In an embodiment, the prefilter may include a first layer formed from a reticulated foam or an open cell foam. For example, the first layer may be formed from a reticulated polyurethane (PU) foam. In some embodiments, the prefilter may also include a second layer. In such embodiments, the first layer may be laminated to the second layer, wherein the prefilter may be attached to the distal-wall by heat sealing the second layer to an inner surface of the distal-wall. The second layer may be formed from a polyester nonwoven or a spunbond-meltblown-spunbond polypropylene (SMS PP) nonwoven.

In an embodiment, the filter assembly may comprise a membrane layer, a backing layer, and a filter media arranged therebetween. The filter assembly may be attached to an outer surface or of the one of the body-side wall and the distal-side wall or an inner surface of the one of the body-side wall and the distal-side wall, such that the membrane layer covers the outlet. The backing layer may be formed from a low density polyethylene film. The filter media may be formed from an activated carbon impregnated foam, which may be hydrophobic. In an embodiment, the filter media may be formed from an activated carbon reticulated PU foam. The membrane layer may be formed from a SMS PP nonwoven. In an embodiment, the SMS PP nonwoven may have a basis weight of about 40 gsm to about 80 gsm.

In an embodiment, the filter assembly may be configured to provide a radial gas flow path through the filter media. In such an embodiment, the filter assembly may be configured to direct the gas egressing through the pouch outlet to flow through the membrane layer and radially flow through the filter media and exit the filter assembly through at least one gas outlet provided proximate an outer periphery of the filter assembly.

In an embodiment, the filter assembly and the multi-stage protection may be configured and arranged to allow the gas collected in the collection area to flow through microperforations of the protective panel and flow through the prefilter and exit the ostomy pouch through the outlet and flow through the membrane layer and filtered via the filter media before exiting the filter assembly.

In another embodiment, the filter assembly and the multi-stage protection may be configured and arranged to allow the gas collected in the collection area to flow through microperforations of the protective panel, flow through the prefilter, and flow through the filter media radially, and flow through the membrane layer before exiting the ostomy pouch through the outlet.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
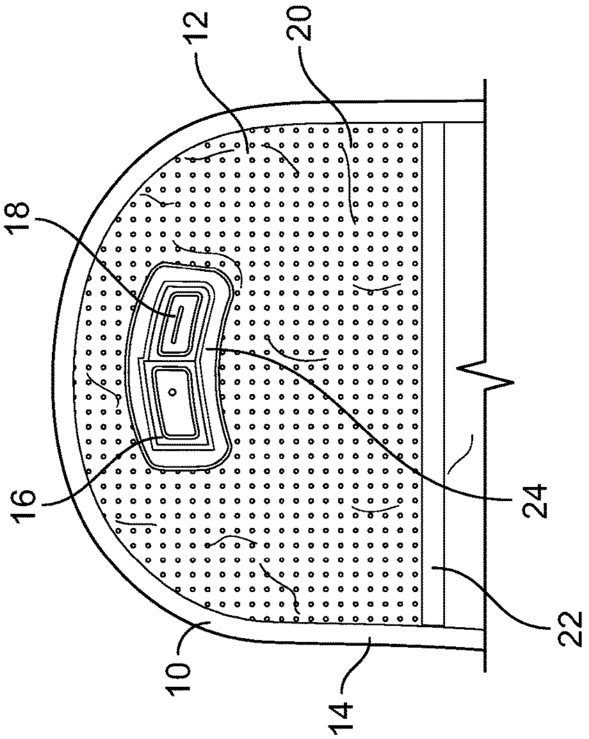
FIG. 1 is a perspective view of an ostomy appliance comprising a filter assembly and a multi-stage filter protection according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 shows an ostomy appliance 10 according to an embodiment. The ostomy appliance 10 may be an ostomy pouch. The ostomy appliance 10 may include outer walls 12 comprising a body-side wall and a distal-side wall joined together at an outer periphery 14. The outer walls 12 may define an interior volume, which according to one embodiment, may include a collection area. The ostomy appliance 10 may also include a filter assembly 16 attached to one of the outer walls 12 over a gas outlet provided therein. The filter assembly 16 may be fluidically connected to the collection area to allow gas to flow through the filter assembly 16 and exit through the gas outlet. The filter assembly 16 may include a filter media 18 comprising a charcoal, carbon or other suitable deodorizing material for deodorizing gas passing therethrough.

The ostomy appliance 10 may include a multi-stage protection to reduce a risk of ostomy effluent clogging the filter assembly 16 and cause ballooning of the ostomy pouch. In an embodiment, the ostomy appliance 10 may include a two-stage protection comprising a protective panel 20 and a prefilter 24. A first stage protection may be the protective panel 20 arranged between two opposing outer walls 12. In the embodiment of FIG. 1, the filter assembly 16 may be attached to an upper portion of the distal-side wall. In this embodiment, the protective panel 20 may be arranged in an upper portion of the ostomy appliance 10 and sealed to the opposing outer walls 12 along the peripheral seal 14. The protective panel 20 may also be sealed to the distal-side wall along a lower periphery providing a horizontal seal 22.

Figure 3:
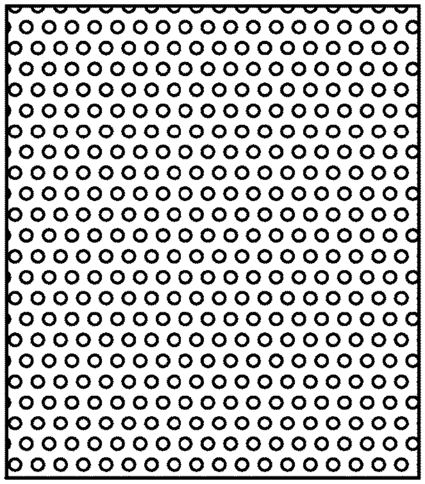
FIG. 3 is an illustration of a microperforated protective panel according to an embodiment.

The protective panel 20 may be formed from a perforated film configured to block ostomy effluent while allowing gas to flow therethrough. In an embodiment, the protective panel 20 may comprise a plurality of microperforations having a micro unit sized perforations as shown in FIG. 3. In some embodiments, the protective panel 20 may comprise perforations of various sizes and/or perforations in various patterns. For example, the protective panel 20 may comprise microperforations in a lower portion and may be free of perforation in an upper portion proximate the filter assembly 16.

Figure 4:
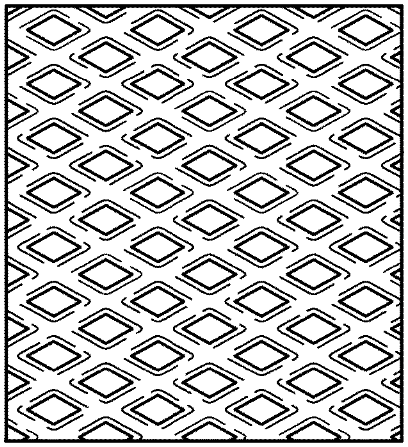
FIG. 4 is an illustration of an embossed protective panel comprising a diamond-shaped pattern according to an embodiment.

In another embodiment, the protective panel 20 may be formed from a textured film and arranged to protect the filter assembly 16. For example, the protective panel 20 may be formed from an embossed film configured to block ostomy effluent while allowing gas flow through. The embossed film may also be configured to minimize pancaking of the ostomy bag, wherein the protective panel 20 is arranged to prevent the outer walls 12 from stick together and to facilitate ostomy effluent to drop to the bottom of the ostomy pouch. The protective panel 20 may be embossed in various patterns, various depths, and/or at various locations. In an embodiment, the protective panel 20 may be embossed in a diamond-shaped pattern as shown in FIG. 4. The diamond-shaped pattern may be configured to define diagonal channels providing gas paths to the filter assembly 16. The diagonal channels may be configured to reduce a risk of the gas paths being blocked by ostomy effluent. Such diagonal channels may be less likely to be blocked than straight vertical and horizontal channels, such as those defined in a checkerboard pattern. In an embodiment, the protective panel 20 may be formed from a textured film that is free of textures in at least a portion of the textured film proximate a prefilter 24. The protective panel 20 may include a gas inlet opening or may be attached to the outer wall 12 discontinuously to provide a gas flow path.

Figure 5:
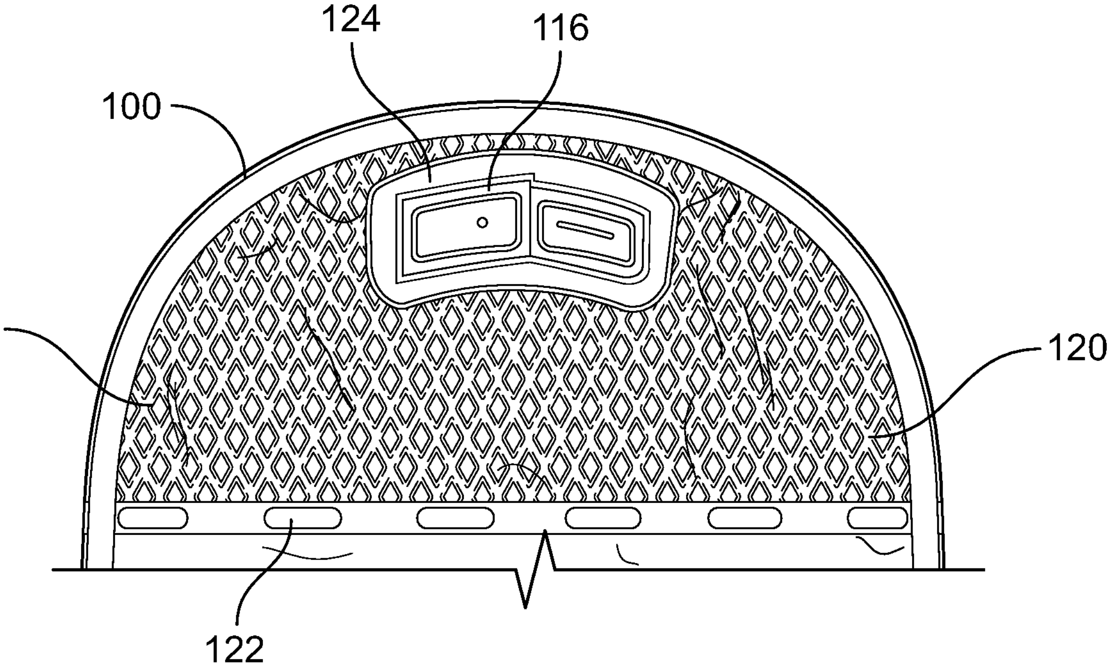
FIG. 5 is a perspective view of an ostomy pouch comprising a filter assembly and a multi-stage filter protection according to an embodiment.

FIG. 5 is a partial perspective view of an ostomy pouch 100 according to an embodiment. The ostomy pouch 100 may be configured similar to the ostomy pouch 10 generally comprising a filter assembly 116 and a two-stage protection including a protective panel 120 and a prefilter 124. In this embodiment, the protective panel 120 may be formed from an embossed film comprising a diamond shaped pattern, which may be sealed to a pouch wall 112 via a discontinuous heat seal 122 to provide a gas flow path.

In an embodiment, the protective panel 20 may be formed from an embossed and perforated film. For example, the protective panel 20 may be formed from an embossed film comprising a plurality to microperforations. In such an embodiment, the protective panel 20 may be free of textures and perforations proximate the prefilter 24.

In some embodiments, the protective panel 20 may include at least one slit or cut in a lower portion to allow any ostomy effluent accumulated between the protective panel 20 and the outer wall 12 to flow down to the collection area. In an embodiment, the protective panel 20 may include a first set of microperforations arrange proximate a lower periphery of the protective panel 20 and a second set of microperforations arranged thereabove, wherein the first set of microperforations have a diameter larger than that of the second set of microperforations. In such an embodiment, the first set of microperforations may be configured to allow ostomy effluent accumulated between the protective panel 20 and the outer wall 12 to flow down to the collection area.

Figure 2:
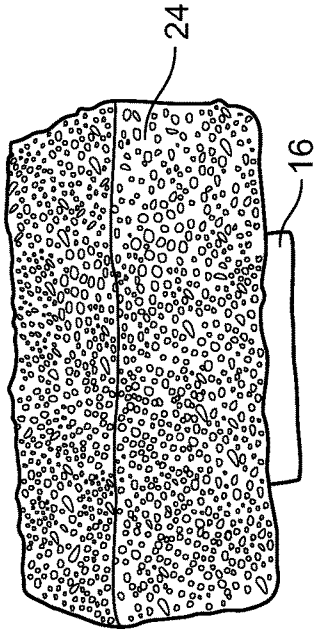
FIG. 2 is a schematic cross-sectional illustration of a foam prefilter arranged adjacent a filter assembly according to an embodiment.

A second stage filter protection may be provided by the prefilter 24. FIG. 2 is a schematic cross-sectional illustration of the prefilter 24 provided adjacent the filter assembly 16 (the thickness of the prefilter 24 is exaggerated). The prefilter may be formed from a suitable material configured to restrict ostomy effluent including thinner (lower viscosity) effluent while allowing gas to flow therethrough. Suitable prefilter materials include, but are not limited to, foams, such as a reticulated open cell foam, textiles, microfleece, non-woven, and the like. Some of the suitable prefilter materials, such as a polyurethane foam, textile, and microfleece may be a hydrophobic material that may repel liquid ostomy effluent away from the prefilter 24.

In an embodiment, the prefilter 24 may be formed from a reticulated polyurethane foam. The foam may have a pore size of about 10 pores per inch (ppi) to about 250 ppi, preferably about 30 ppi to about 200 ppi. For example, the foam may have a pore size of about 40 ppi to about 60 ppi. In the embodiment of FIGS. 1 and 2, the prefilter 24 may be sized and arranged to approximately cover the filter assembly 16. In another embodiment, the prefilter 24 may be sized substantially larger than the filter assembly 16. In yet another embodiment, the prefilter 24 may be arranged to substantially fill a compartment defined between the protective panel 20 and the distal-side wall. The prefilter 24 may be relatively thin to minimize the bulkiness of the ostomy appliance 10. In an embodiment, the prefilter 24 may be formed from an open-cell foam having a thickness of about 1/32 inches to about 1/2 inches, preferably about 1/16 inches to about 1/4 inches, and more preferably about 1/8 inches. The prefilter 24 may be configured such that a user may squeeze out liquid absorbed therein by applying pressure through pouch outer walls.

In some embodiments, the ostomy appliance 10 may include more than two stages of filter protection. For example, the ostomy appliance 10 may include at least one heat seal, which may be configured and arranged to protect the filter assembly 16. In an embodiment, the ostomy appliance 10 may include at least one heat seal that seals the protective panel 20 to one of the outer walls 12 proximately below the filter assembly 16 or surrounding a lower portion of the filer assembly 16 to deter ostomy effluent from reaching the filter assembly 16 and/or the prefilter 24.

Figure 6:
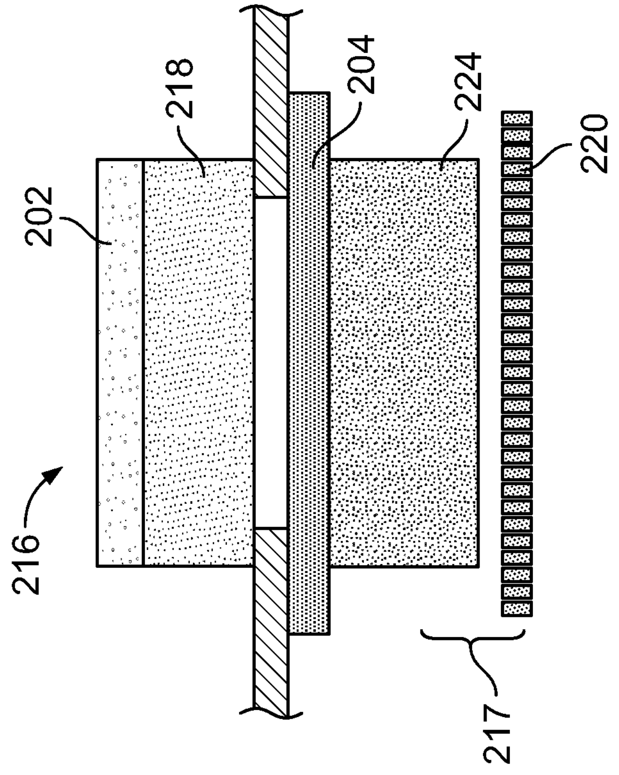
FIG. 6 is a schematic illustration of a filter assembly and a multi-stage filter protection according to another embodiment.

FIG. 6 is a schematic illustration of a filter assembly 216 and a multi-stage filter protection 217 according to an embodiment. In this embodiment, the filter assembly 216 may comprise a backing layer 202 and an activated carbon foam filter media 218. The multi-stage filter protection 217 may comprise a membrane layer 204, a prefilter 224 formed from a foam material, and a protective panel 220 formed from a microperforated film. The membrane layer 204, which may be formed from a suitable gas permeable material, may be arranged between the filter media 218 and the prefilter 224. The suitable gas permeable material for the membrane layer 204 may include, but are not limited to, membrane materials, gas permeable polymeric films, nonwovens, and the like.

Figure 7:
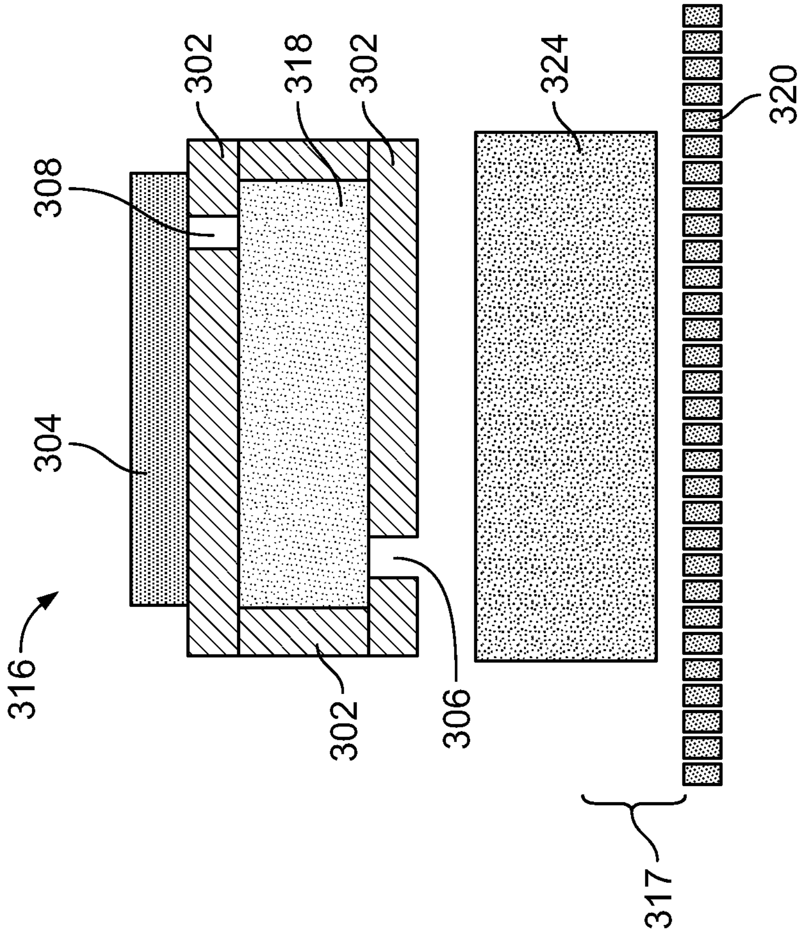
FIG. 7 is a schematic illustration of a filter assembly with a multi-stage filter protection according to yet another embodiment.

FIG. 7 is a schematic illustration of a filter assembly 316 and a multi-stage filter protection 317 according to another embodiment. In this embodiment, the filter assembly 316 may comprise a membrane layer 304 and an activated carbon polyester (PET) filter media 318 enclosed in a packet film 302 formed from a gas impermeable material, wherein a gas inlet opening 306 and a gas outlet opening 308 are provided in the packet film 302. The multi-stage filter protection 317 may comprise a foam prefilter 324 and a microperforated film protective panel 320.

Figure 8:
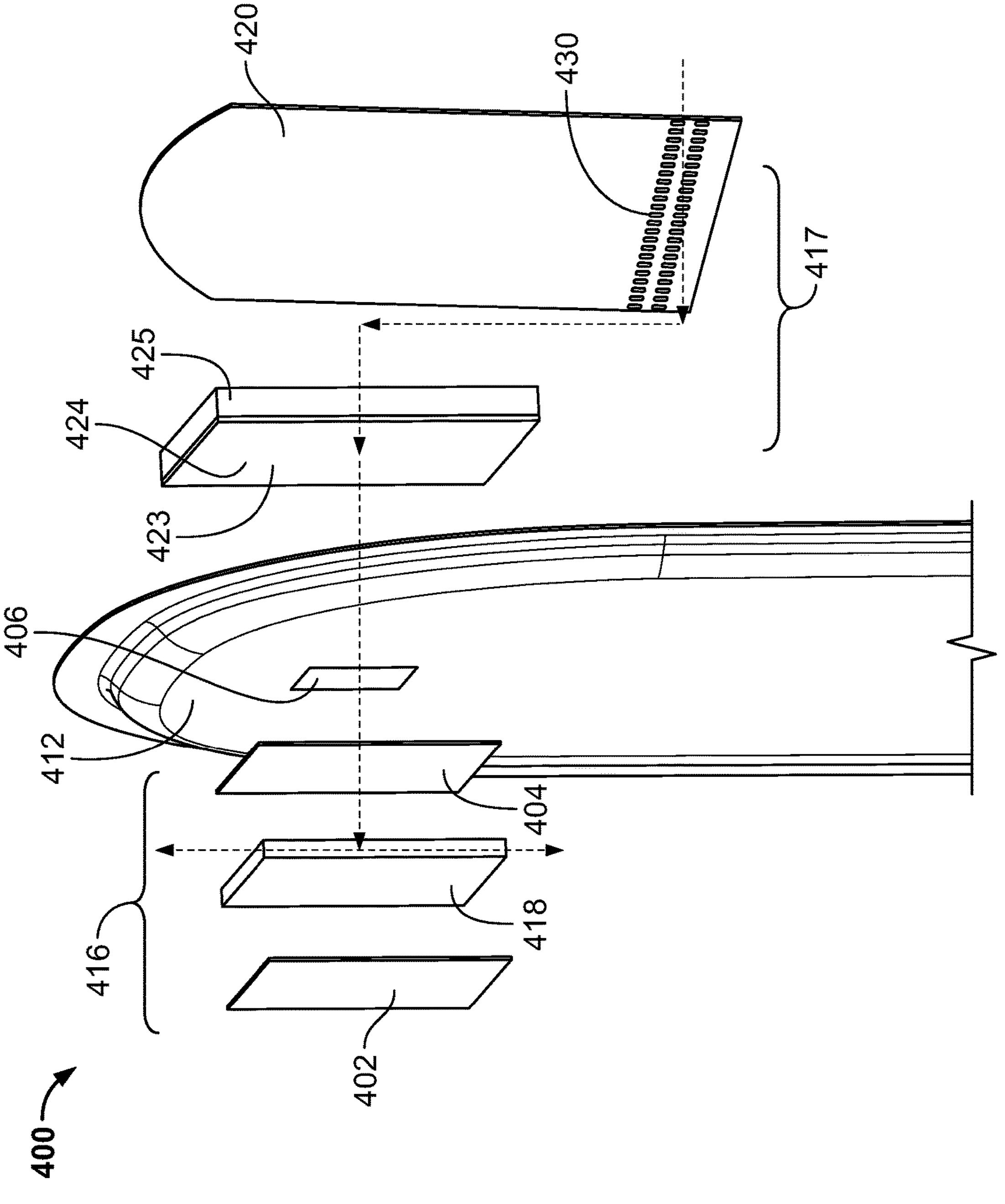
FIG. 8 is a partial exploded view of an ostomy pouch comprising a filter assembly and a multi-stage filter protection according to an embodiment.
Figure 18:
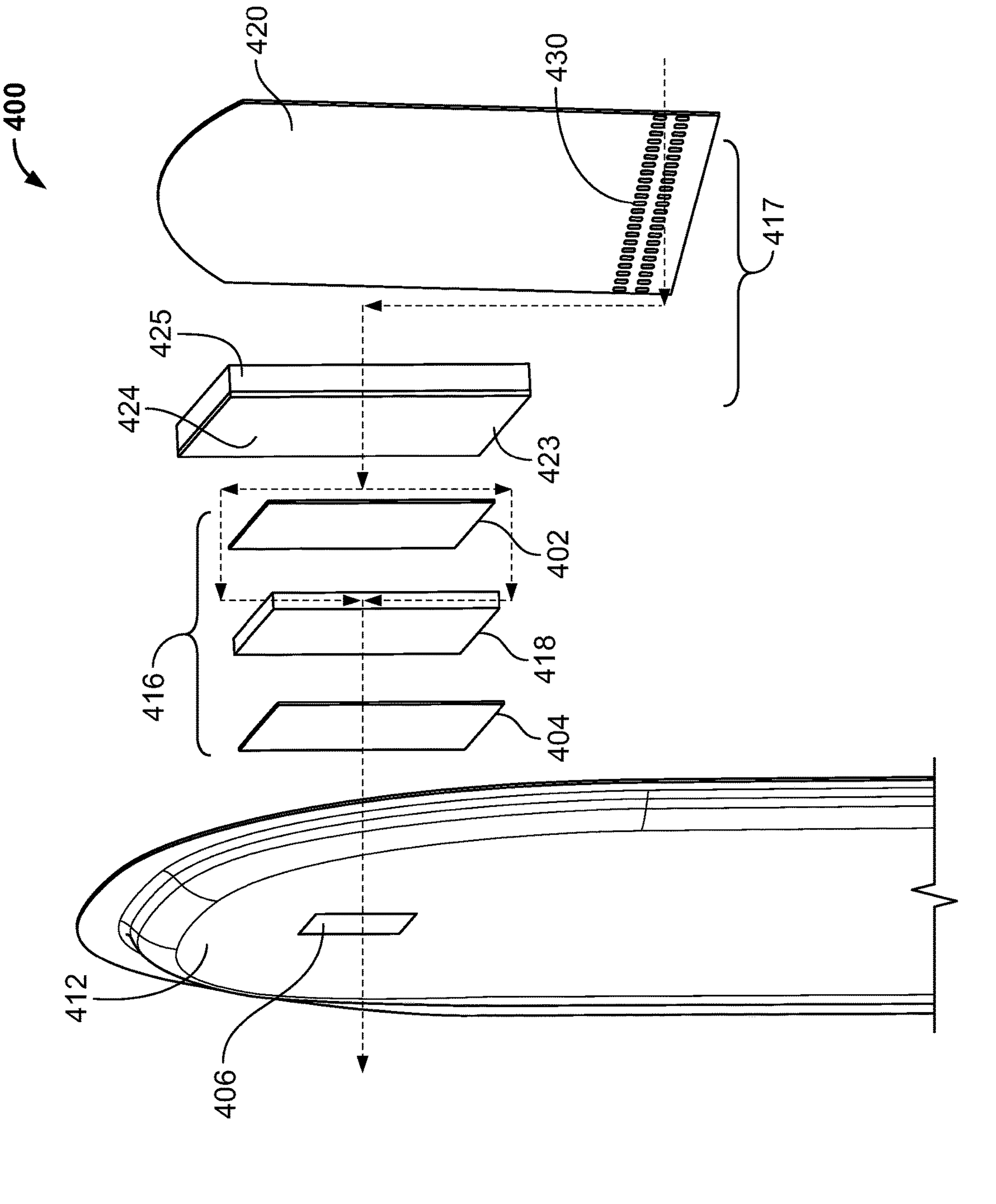
FIG. 18 is a partial exploded view of an ostomy pouch comprising a filter assembly and a multi-stage filter protection according to another embodiment.

FIG. 8 is a partial exploded view of an ostomy pouch 400 according to an embodiment. The ostomy pouch 400 may be configured similar to the ostomy pouch 10 generally comprising a filter assembly 416 and a multi-stage protection 417 including a protective panel 420 and a prefilter 424. In this embodiment, the filter assembly 416 may be attached to an outer surface of a pouch wall 412 while the multi-stage protection 417 may be arranged inside the pouch. In another embodiment, the filter assembly 416 and the multi-stage protection 417 may be arranged inside the pouch as shown in FIG. 18.

The filter assembly 416 may comprise a backing layer 402, a filter media 418, and a membrane layer 404. The filter assembly 416 may be arranged to cover a gas outlet opening 406 defined in the pouch wall 412 and attached to the pouch wall 412, for example via heat sealing. The membrane layer 404 may be formed from a suitable gas permeable material configured to allow gas to flow therethrough while providing protection against ostomy effluent. The filter media 418 may be formed from a suitable filter material configured to deodorize ostomy gas. The backing layer 402 may be formed from a suitable material that has a relatively low gas permeability or gas impermeable and configured to direct gas to flow radially through the filter assembly 416. In this embodiment, gas collected in the ostomy pouch 400 may egress through the outlet opening 406 and flow into the filter assembly 416 through the membrane layer 404 and radially flow through the filter media 418 before exiting the filter assembly 416 as indicated by arrows in FIG. 8. The filter assembly 416 may comprise at least one gas outlet proximate a periphery of the filter assembly 416. For example, the filter assembly 416 may comprise a gas outlet defined by an unsealed periphery.

The radial gas flow length through the filter media 418 may be affected by the size of the outlet opening 406 and the size of the filter media (larger the outlet opening 406, shorter the gas path through the filter media 418). Further, the flow rate of gas egressing the ostomy pouch 100 through the filter assembly 116 may be adjusted by configuring the size of the outlet opening 106 and gas flow properties of the membrane layer 104, such as a porosity of the membrane layer 104. In an embodiment, the size of the outlet opening 406 and the membrane layer 404 may be configured to allow sufficient gas egress to minimize pouch ballooning while still providing a gas flow length through the filter media 418 for excellent odor deodorization.

In an embodiment, the outlet opening 406 may have an area of about 0.02 inch$^2$ to about 0.15 inch$^2$, preferably about 0.05 inch$^2$ to about 0.08 inch$^2$, and more preferably 0.06 inch$^2$ to about 0.07 inch$^2$.

The outlet opening 406 may be provided in various shapes, for example, circular opening, elliptical opening, rectangular opening, square opening, etc. In an embodiment the outlet opening 406 may be defined by a square shaped opening having an area of about 0.0625 inch$^2$ (0.25 inches× 0.25 inches).

Suitable materials for the backing layer 402 may include, but are not limited to, polymeric films having a substantially lower gas permeability compared to the filter media 418. For example, the backing layer 402 may be formed from a polymeric film, such as a low density polyethylene (LDPE) film. The backing layer 402 may have a thickness of about 2 mil to about 10 mil, preferably about 3 mil to about 7 mil, and more preferably about 5 mil.

Figure 10:
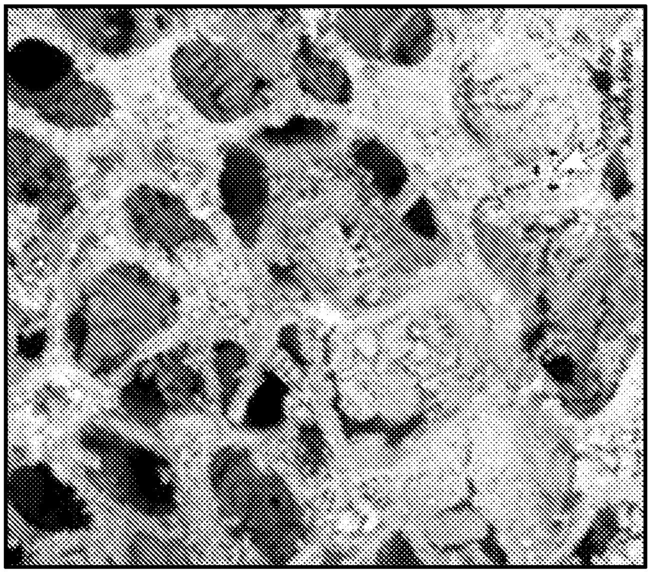
FIG. 10 is a microscopic image of a reticulated foam filled with activated carbon according to an embodiment.
Figure 9:
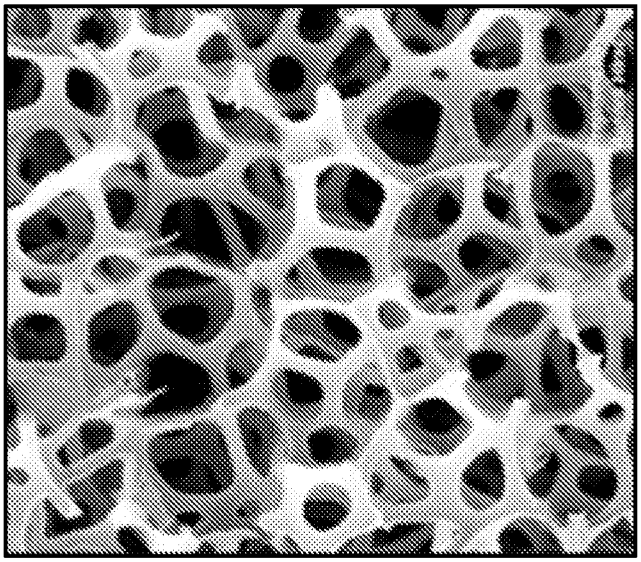
FIG. 9 is a microscopic image of a reticulated foam according to an embodiment.

The filter media 418 may be formed from a suitable filter material comprising charcoal, carbon or other suitable deodorizing materials for deodorizing gas. Suitable filter materials for the filter media 418 may include, but are not limited to, activated carbon foam materials, such as a filter material comprising a reticulated foam and activated carbon, activated carbon nonwoven, and activated carbon cloth. FIG. 9 is a microscopic image of a reticulated foam according to an embodiment, and FIG. 10 is a microscopic image of a reticulated foam filled with activated carbon according to an embodiment. The filter media 418 may have a thickness of about 0.03 inches to about 0.15 inches, preferably about 0.06 inches to about 0.12 inches, and more preferably about 0.07 inches to about 0.1 inches.

In an embodiment, the filter media 418 may be formed from a reticulated polyurethane (PU) foam comprising activated carbon and having a thickness of about 0.089 inches, such as PU foam filter materials available from Freudenberg. Such a PU foam filter material may be hydrophobic and may provide additional advantages for the filter assembly 416 arranged on an outer surface of the pouch. For example, the hydrophobic filter media 418 may resist water and eliminate a need for a filter sticker when the filter assembly 416 is exposed to water, for example during shower or swimming.

The membrane layer 404 may be formed from a suitable gas permeable material. Suitable gas permeable materials for the membrane layer 404 may include, but are not limited to, ePTFE (expanded polytetrafluoroethylene) membrane, UHMW PE (ultra high molecular weight polyethylene) membrane, pulp/polyester membrane, spunmelt PP (polypropylene) membrane, SMS PP (spunbond meltblown spunbond polypropylene) nonwoven, and the like. The membrane layer 404 may have a thickness of about 0.5 mil to about 15 mil, preferably about 0.8 mil to about 12 mil. In an embodiment, the membrane layer 404 may be formed from a tri-laminate SMS PP nonwoven comprising a spunbond PP top layer, a meltblown PP middle layer, and a spunbond PP bottom layer having a basis weight of about 10 gsm to about 500 gsm, preferably about 30 gsm to about 120 gsm, and more preferably about 40 gsm to about 80 gsm. For example, the membrane layer 404 may be formed from a SMS PP nonwoven having a basis weight of about 44 gsm available under Style T063-73960 from Precision Fabrics Group Inc. In another embodiment, the membrane layer 104 may be formed from a microporous UHMW PE membrane having a basis weight of about 1 gsm to about 20 gsm, preferably about 2 gsm to about 5 gsm, a thickness of about 10 μm to about 50 μm, preferably about 15 μm to about 40 μm, and a porosity of about 60% to about 90%, preferably about 70% to about 85%. For example, the membrane layer 104 may be formed from a microporous UHMW PE membrane having a basis weight of about 3 gsm, a thickness of about 20 μm, and a porosity of about 83%, which is available under the tradename Solupor® membranes 3P07A from Lydall Performance Materials B.V.

In an embodiment, the filter assembly 416 may be configured to minimize ballooning while still providing excellent odor filtration and preventing ostomy effluent leakage. Such properties of a filter assembly may be evaluated by analyzing airflow rate through the filter assembly, liquid hold-out, which measures a pressure at which a liquid is forced through a membrane layer of the filter assembly, and deodorization data.

In the embodiment of FIG. 8, the airflow rate and liquid hold-out of the filter assembly 416 may be mainly determined by the properties of the membrane layer 404. The cost of the membrane layer for many prior art filter assemblies, for example, those including a membrane layer formed from an ePTFE membrane or UHMW PE membrane, is often the largest portion of the total material cost of the filter assembly. For example, the cost of the membrane layer formed from an ePTFE membrane may make up over 50% of the total material cost of a filter assembly.

The inventors of the present application have researched and analyzed numerous different membrane materials, nonwoven materials, fabric materials, and other gas permeable materials to identify a suitable material for a filter membrane layer that can provide comparable or better filter properties at a substantial cost saving. After substantial time and investment in research and development, it was discovered that a filter assembly comprising a membrane layer formed from a SMS PP nonwoven material, which is typically used for hospital gowns, may provide surprisingly excellent filter membrane properties, such as airflow rate and liquid hold-out, at a substantially lower cost. For example, the cost of a SMS PP nonwoven material can be as low as about 1% of the cost of an ePTFE membrane material. Airflow rate and liquid hold-out data for various membrane materials are shown in Table 1.

TABLE 1

Airflow Rate and Liquid Hold-Out Data of Filter Membranes

| Membrane | Airflow rate @0.18 psi (cc/s) | Liquid ($H_2O$) hold-out (psi) |
|---|---|---|
| SMS PP nonwoven (T063-73960, PFG) | 28.6 (filter assembly) | 1.32 (membrane only) |
| Spunmelt PP | 22.4 (filter assembly) | 0.7 (membrane only) |
| Pulp/polyester | 20.9 (filter assembly) | 0.27 (filter assembly) |
| UHMW PE (Solupor ® 3P07A, Lydall) | 8.06 (membrane only) | 4 (membrane only) |
| e-PTFE | 11.2 (filter assembly) | 6 (filter assembly) |
| e-PTFE | 7.28 (filter assembly) | 6 (filter assembly) |
| UHMW PE | 4.1 (filter assembly) | >10 (filter assembly) |

The airflow rate was tested using Isaac HD Multi-Function Leak Tester (Isaac tester) equipped with a Mass Flow Meter (MFM), which measures a mass flow rate of air through a pouch to maintain a specified pressure. A square shaped and Teflon coated test plate including alignment holes near each of the corners and an opening in the center to allow air to pass into a pouch was used to mount a pouch. A test fixture including two air cylinders was used to clamp the test plate and the pouch mounted thereto. The test fixture included a hole defined therein to allow air to pass from a pressure transducer into the pouch.

Figure 11:
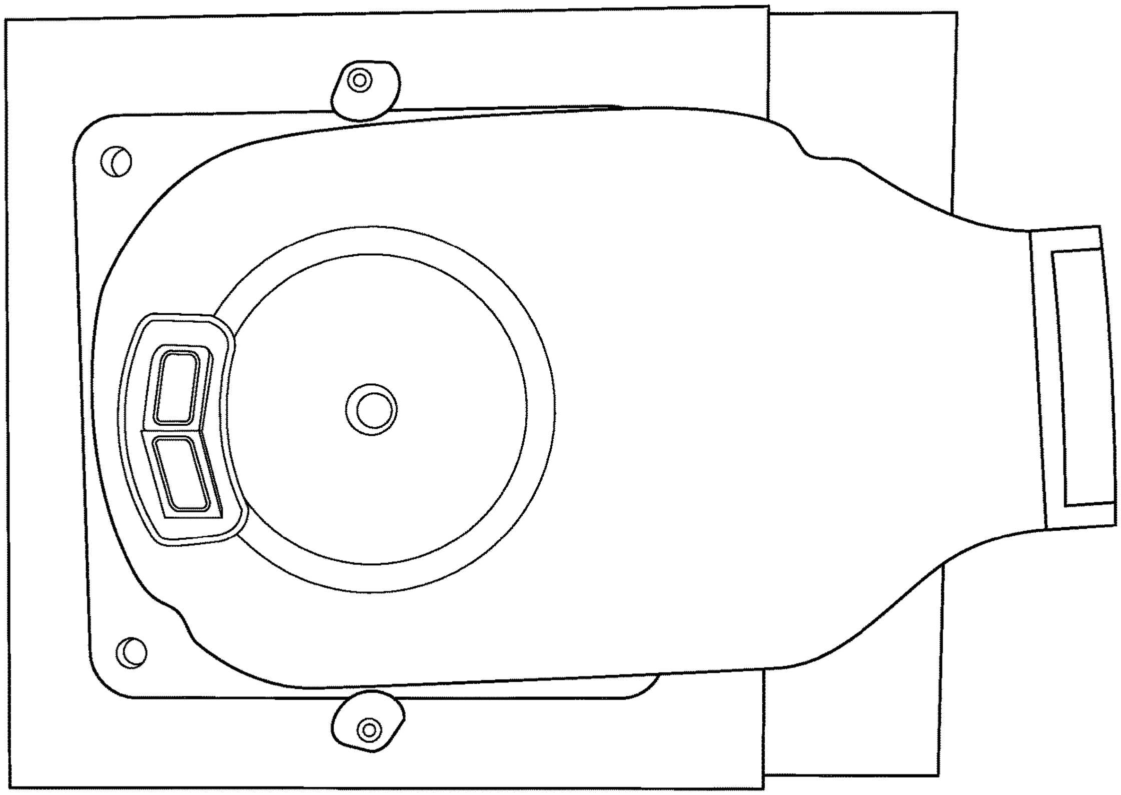
FIG. 11 is an illustration of an ostomy pouch mounted on a test fixture for an airflow rate test according to an embodiment.

The airflow rate data in Table 1 were collected by measuring an air flow rate to maintain a 0.18 psi pressure in a sample pouch including a filter assembly or a membrane (as indicated in Table 1) attached thereto to cover a gas outlet opening. The sample pouch was attached to the test plate by removing a barrier backing and centering a pouch starter hole over the center hole of the test plate, such that no air channels are formed between the barrier and the test plate. The test plate with the pouch mounted thereto is attached to the test fixture using the locating pins to guide alignment and pneumatically clamped as shown in FIG. 11. Using the Isaac tester, an air flow rate to maintain a pressure of 0.18±0.018 psi was measured and recorded.

Figure 12:
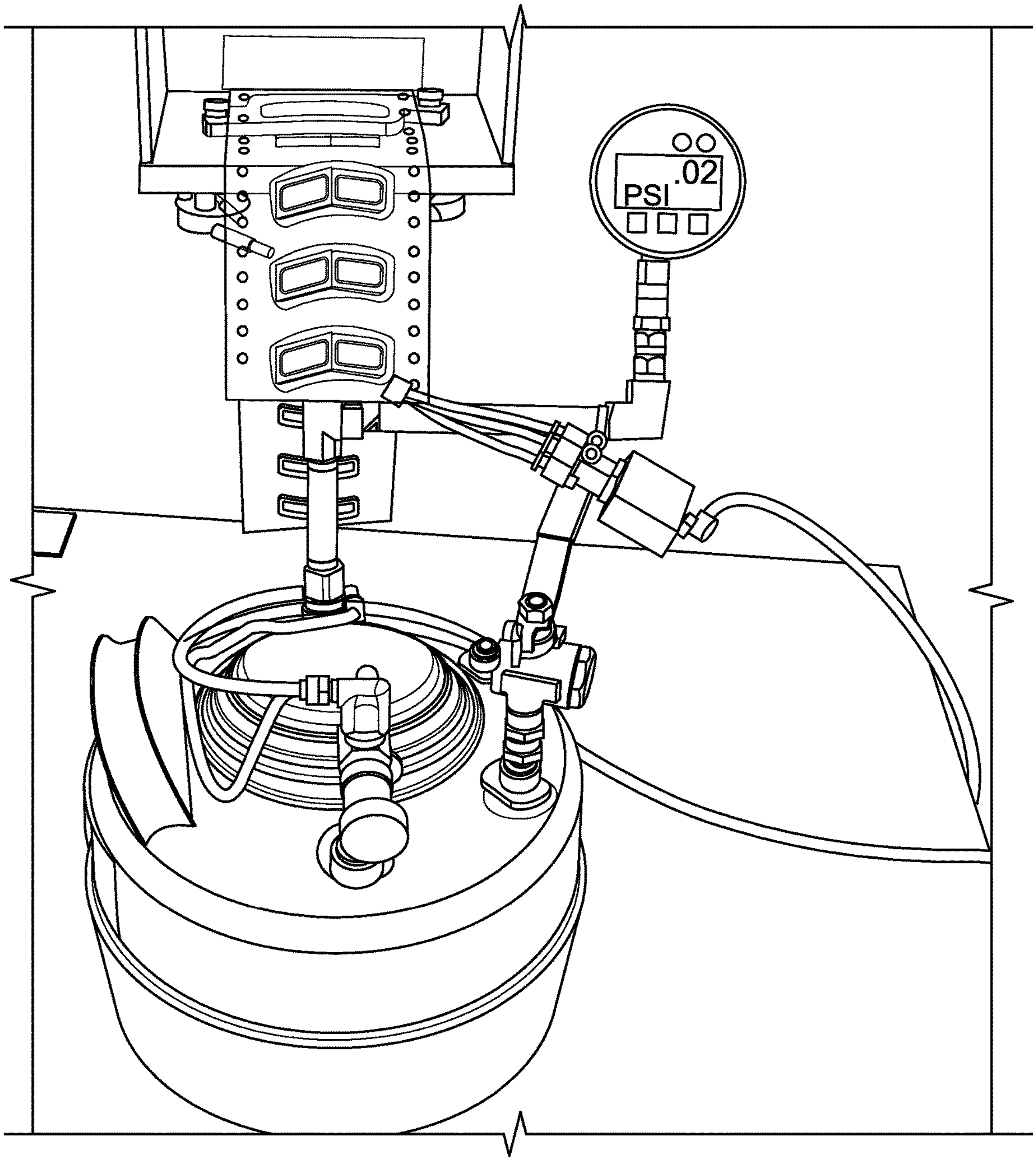
FIG. 12 is an illustration of a liquid hold-out test set up according to an embodiment.
Figure 13:
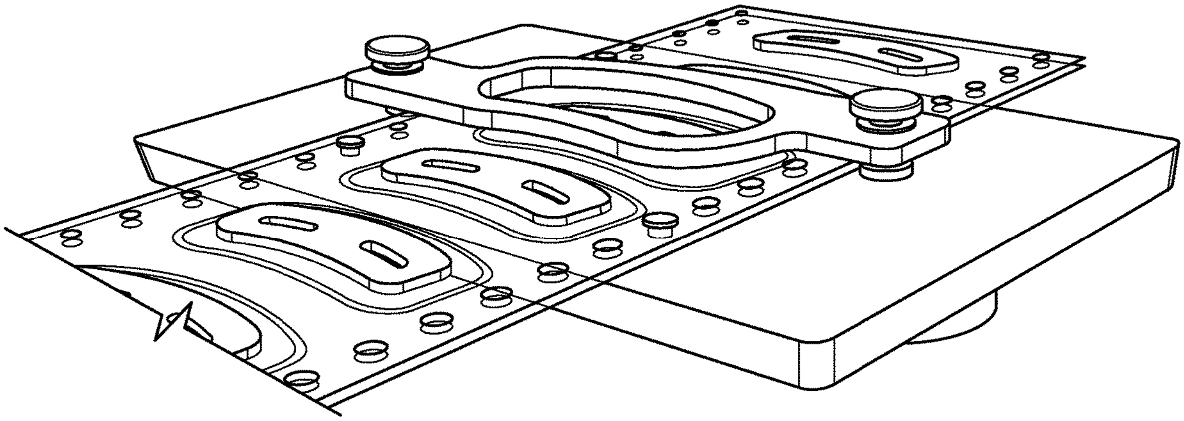
FIG. 13 is an illustration of an ostomy filter clamped in a test fixtured in the liquid hold-out test set up of FIG. 12.

The liquid hold-out was tested using a test equipment system including a liquid pressure tank, an air source, and a liquid pressure gauge (FIG. 12) to measure a pressure at which a liquid (water was used for the data provided in Table 1) is forced through a membrane or a membrane layer of a filter assembly. A sample membrane or a sample filter assembly (as indicated in Table 1) was placed on a fixture and a filter clamp was positioned over the fixture, such that the filter clamp is aligned over the membrane or filter assembly as shown in FIG. 13. After closing the filter clamp via a pneumatic valve, the system pressure was raised until water penetrated the sample membrane or the membrane layer of the sample filter assembly.

After detailed examination and careful studies of ostomy pouch ballooning phenomenon, effluent leakage through ostomy filters, and filtering of ostomy gas, and analyses of airflow rate and liquid hold out data of numerous membrane materials and filter assemblies, it was discovered that an ostomy pouch comprising a filter assembly configured to have an airflow rate @ 0.18 psi of greater than about 10 cc/s and less than about 40 cc/ss and a liquid (water) hold-out of greater than about 0.9 psi may minimize pouch ballooning while still preventing ostomy effluent leakage.

In an embodiment, the filter assembly 416 may comprise the backing layer 402 formed from a LDPE film having a thickness of about 5 mil, the filter media 418 formed from an activated carbon reticulated PU foam having a net density of about 26 kg/$m^3$ to about 30 kg/$m^3$ (tested according to ISO 845), and the membrane layer 404 formed from a SMS PP nonwoven having a basis weight of about 44 gsm, wherein the filter assembly 416 may be covering the outlet opening 406 having an area of about 0.06 inch$^2$ to about 0.07 inch$^2$ and configured to have an airflow rate @0.18 psi of greater than about 10 cc/s and less than about 40 cc/s and a liquid (water) hold-out of greater than about 0.9 psi and less than about 3.0 psi. In an embodiment, the filter assembly 416 may be configured to cover the outlet opening 406 having an area of about 0.0625 inch$^2$ and have an airflow rate @0.18 psi of greater than about 15 cc/s and less than about 35 cc/s and a liquid (water) hold-out of greater than about 1.0 psi and less than about 2.0 psi. The filter assembly 416 may be provided in various shapes, for example, circular, elliptical, rectangular, or square shapes.

Figure 16:
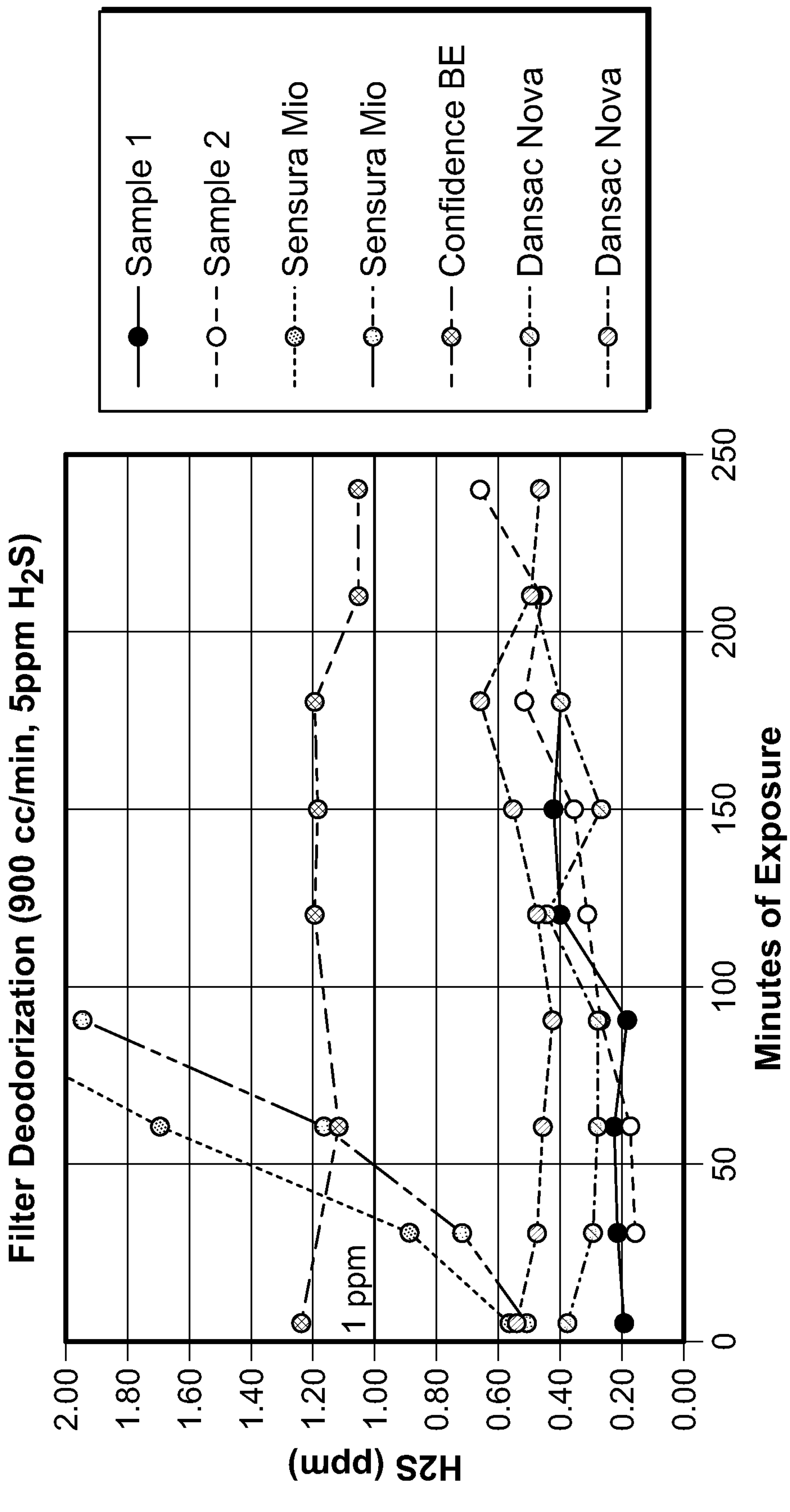
FIG. 16 is a graph of volatile analysis test results using $H_2S$ challenge gas.
Figure 17:
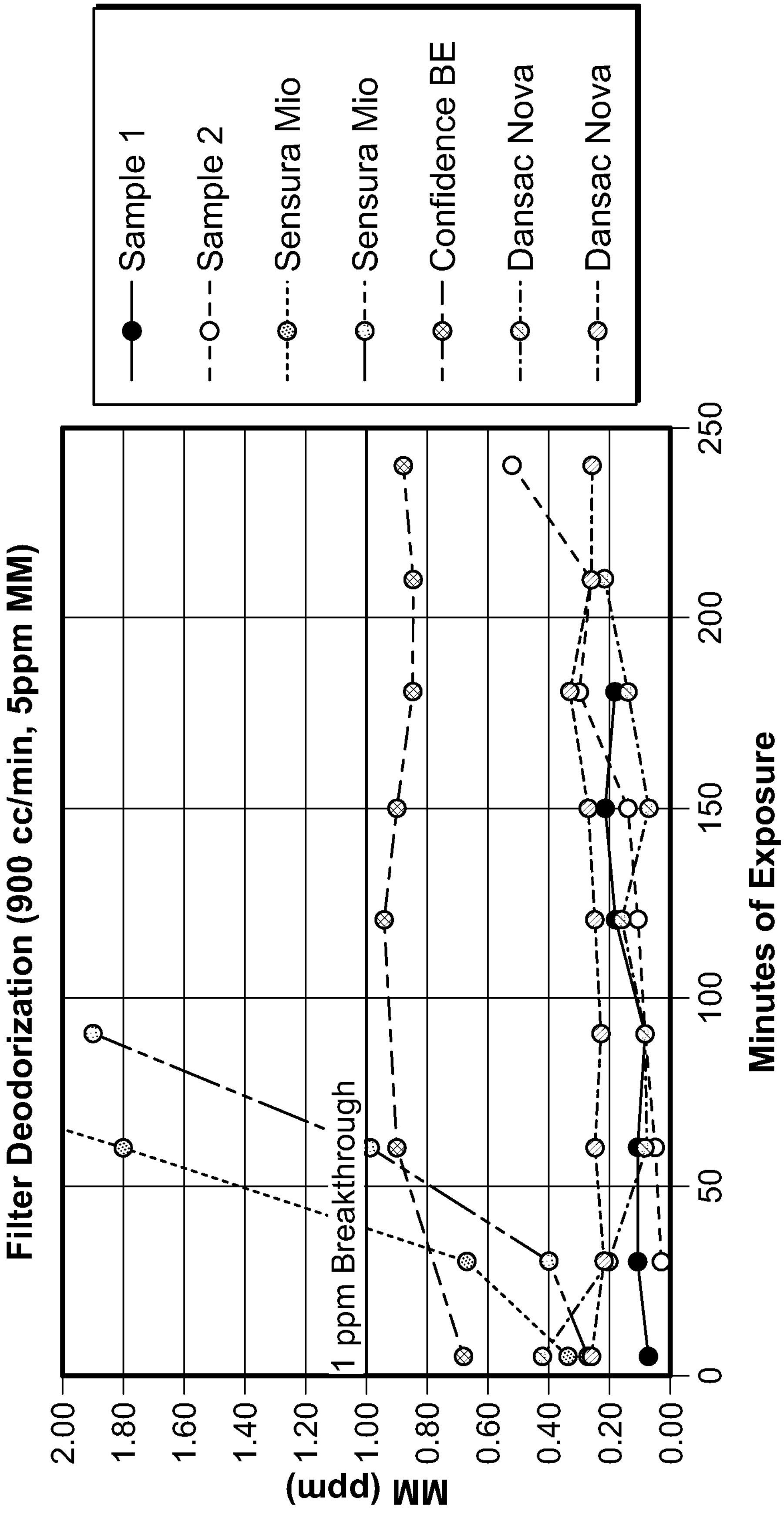
FIG. 17 is a graph of volatile analysis test results using methyl mercaptan challenge gas.

Samples of the filter assembly 416 having a square-shaped body with the side length of 1.165 inches and comprising the backing layer 402 formed from a LDPE film having a thickness of about 5 mil, the filter media 418 formed from an activated carbon reticulated PU foam having a net density of about 26 kg/$m^3$ to about 30 kg/$m^3$ (tested according to ISO 845), and the membrane layer 404 formed from a SMS PP nonwoven having a basis weight of about 44 gsm were prepared and tested for deodorization properties along with prior art filter assemblies. Volatile analyses using a challenge gas containing 5 ppm $H_2S$ in dry nitrogen and a challenge gas containing 5 ppm methyl mercaptan (MM) in dry nitrogen were conducted. The test parameters included: challenge gas humidified to 25% RH (relative humidity), a flow rate of challenge gas to filter of 15 cc/s, and a back pressure of 0.8 psi. FIG. 16 is a graph of volatile analysis test results using the $H_2S$ challenge gas, and FIG. 17 is a graph of volatile analysis test results using the MM challenge gas. As shown in FIGS. 16 and 17, the samples of the filter assembly 416 (referred to as "Sample 1" and "Sample 2") exhibited better deodorization properties when compared to Coloplast SenSura® Mio filter assembly samples including an e-PTFE membrane and Salts Healthcare Confidence BE® filter assembly samples including an e-PTFE membrane, and exhibited similar deodorization properties when compared to Dansac NovaLife filter assembly samples including a UHMW PE membrane.

Referring back to FIG. 8, the multi-stage filter protection 417 may comprise the prefilter 424 arranged to cover the gas outlet opening 406 and sealed to an inner surface of the pouch wall 412 and the protective panel 420 covering the prefilter 424 and sealed to an inner surface of the pouch wall 412. In such an embodiment, the protective panel 420 may function as a coarse prefilter and a first line of protection and the prefilter 424 may function as a fine prefilter and a second line of protection to provide a multiple protection for the filter assembly 416 from ostomy effluent collected in the pouch.

In an embodiment, the prefilter 424 may comprise a first layer 425 and an optional second layer 423. The first layer 425 may be configured for fine particulate blocking and formed from any suitable material comprising sufficient gas flow path/channels to provide a substantially lower gas flow resistance when compared to the optional second layer 423 or the membrane layer 404. Suitable materials for the first layer 425 may include, but are not limited to, open-cell foams and reticulated foams including about 10 ppi to about 250 ppi, preferably about 30 ppi to about 200 ppi. For example, the first layer 425 may be formed a reticulated foam including about 200 ppi. Suitable materials for the first layer 425 are not limited to foam materials and may include other similar materials configured for fine particular blocking and a relatively low gas flow resistance. The first layer 425 may have a thickness of about 1/32 inches to about ½ inches, preferably about 1/16 inches to about ¼ inches, and more preferably about ⅛ inches. In an embodiment, the first layer 425 may be formed from, a reticulated PU foam having about 45 ppi and a thickness of about ⅛ inches. In some embodiment, the first layer 425 may be laminated to the second layer 423.

The second layer 423 may be formed from a suitable material configured to provide some support for the first layer 425 during handling and processing and heat sealability to the pouch wall 412. Suitable materials for the second layer 423 include, but are not limited to, nonwoven materials, membrane materials, gas permeable polymeric materials and the like. For example, the second layer 423 may be formed from a polyester (PET) nonwoven or a SMS PP nonwoven having a basis weight of about 10 gsm to about 500 gsm, preferably about 20 gsm to about 100 gsm, and more preferably about 30 gsm to about 50 gsm. The prefilter 424 may be configured such that a user may apply pressure through the pouch walls to squeeze out any liquid absorbed by the first layer 425. The second layer 423 is optional. In embodiments where the prefilter 424 does not include the second layer 423, the first layer 425 may be directly sealed to the pouch wall 412.

The protective panel 420 may be formed from a suitable microperforated film and sealed to the pouch wall 412 via a peripheral seal. In an embodiment, the protective panel 420 may be configured and sized slightly larger than the prefilter 423 to cover and seal around the prefilter 423. In other embodiments, the protective panel may be configured to cover about ⅕ to about ⅔ of an upper portion of the ostomy pouch, preferably, about ¼ to about ½ of an upper portion of the ostomy pouch. The microperforated film may be formed from a suitable polymeric material configured for heat sealing to the pouch wall 412. In an embodiment, the protective panel 420 may be formed from a copolymer comprising about 8% ethylene-vinyl acetate (EVA). The protective panel 420 may have a thickness of about 0.5 mil to about 10 mil, preferably about 1 mil to about 5 mil.

The protective panel 420 may comprise microperforations in a portion, in more than one portion or throughout the whole area of the protective panel 420. In the embodiment of FIG. 8, the protective panel 420 may include microperforations 430 only in a lower portion of the protective panel 420. In such an embodiment, gas collected in the ostomy pouch 400 may flow through the microperforations 430 in the lower portion of the protective panel 420 and flow upward through the prefilter 424 and exit the pouch through the gas outlet opening 406 and flow through the membrane layer 404 and filtered via the filter media 418 before exiting the filter assembly 416 as shown by the arrows in FIG. 8.

The protective panel 420 may include microperforations defined by a plurality of generally circular cylindrical openings having a diameter of about 50 μm to about 500 μm, preferably about 100 μm to about 450 μm, more preferably about 150 μm to about 400 μm. In an embodiment, the protective panel 420 may include microperforations in a lower portion of the protective panel 420, wherein the microperforations have a pore-density of about 10 pores per inch (ppi) to about 500 ppi, preferably about 100 ppi to about 300 ppi. In some embodiments, the protective panel 420 may include microperforations of various sizes, various patterns, various shapes, and/or in selected portions of the protective panel 420.

Figure 14:
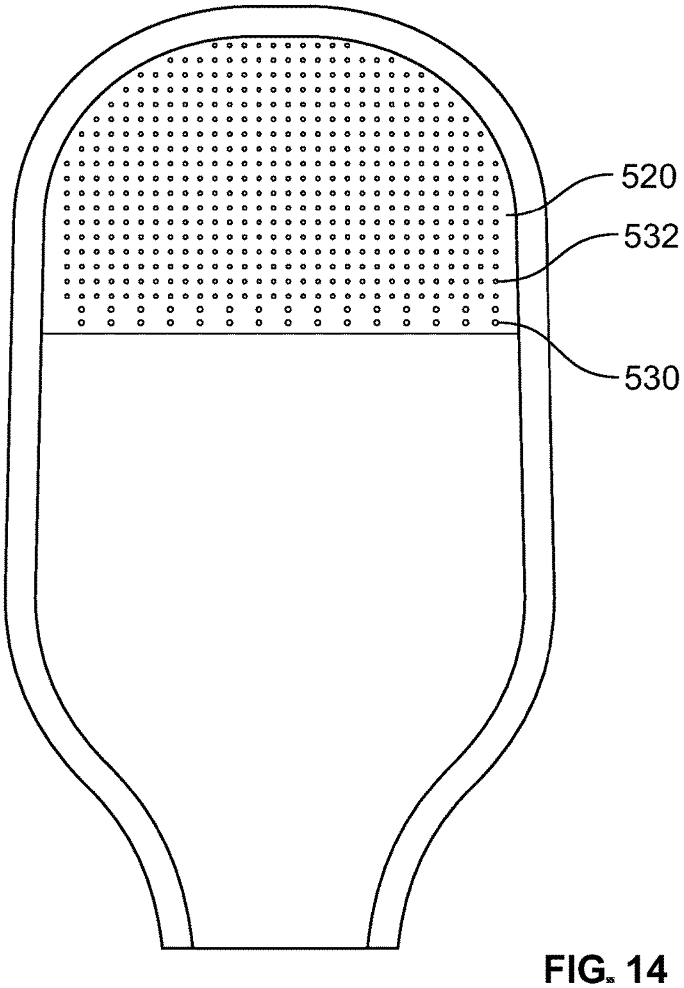
FIG. 14 is a schematic perspective view of an ostomy pouch including a protective panel formed from a perforated film according to an embodiment.
Figure 15A:
FIGS. 15A-15D are schematic illustrations of perforations according to various embodiments.
Figure 15B:
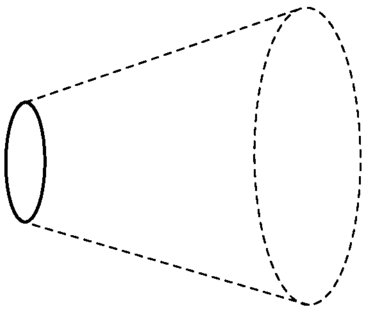
Figure 15C:
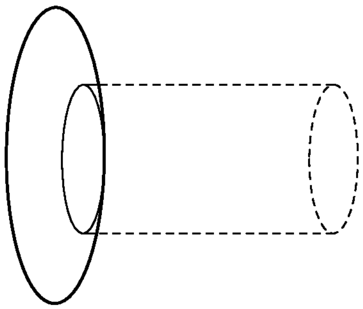
Figure 15D:
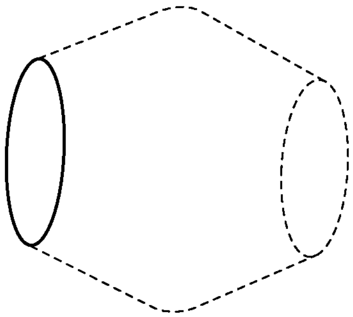

FIG. 14 shows an ostomy pouch comprising a protective panel 520 according to an embodiment, wherein the protective panel 520 includes a first set of microperforations 530 in a lower portion of the protective panel 520 and a second set of microperforations 532 arranged above the first set of microperforations 530. The first set of microperforations 530 may be defined by a plurality of openings having a larger diameter than those of the second set of microperforations 532. For example, the first set of microperforations 530 may be defined by a plurality of generally circular cylindrical openings having a diameter of about 250 μm to about 500 μm, preferably about 300 μm to about 400 μm, and more preferably about 350 μm to about 380 μm. The second set of microperforations 532 may be defined by generally circular cylindrical openings having a diameter of about 50 μm to about 300 μm, preferably about 100 μm to about 250 μm, and more preferably about 125 μm to about 175 μm.

In an embodiment, the protective panel 520 may be formed from a copolymer film containing about 8% EVA and having a thickness of about 2.1 mil and may comprise microperforations, wherein the microperforations include the first set of microperforations 530 defined by a plurality of openings having a diameter of about 380 μm arranged in two rows and the second set of microperforations 532 defined by a plurality of opening having a diameter of about 150 μm arranged in 24 rows, wherein the microperforations have a pore-density of about 100 ppi. The protective panel 520 may be configured for coarse particulate blocking and heat seal to pouch walls along its periphery. In some embodiments, the protective panel 520 may be provided with slits or openings proximate a lower periphery to allow any liquid accumulated between the protective panel and the pouch wall to flow down.

The protective panel may include microperforations formed by openings having various 3D shapes penetrating through the thickness the protective panel, such as the 3D shaped shown in FIGS. 15A-15D.

It is understood that the relative directions described above, e.g, "upward," "downward," "upper," "lower," "above," "below," are used for illustrative purposes only and may change depending on an orientation of the ostomy pouch and/or the patient. Accordingly, this terminology is non-limiting in nature. In addition, it is understood that one or more various features of an embodiment above may be used in, combined with, or replace other features of a different embodiment described herein.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy pouch comprising:

a body-side wall and a distal-side wall joined at an outer periphery and defining an interior volume comprising a collection area;

an inlet for receiving ostomy effluent;

an outlet for egress of gas collected in the collection area;

a filter assembly covering the outlet, wherein the filter assembly comprises a membrane layer, a backing layer, and a filter media arranged therebetween, wherein the filter assembly is attached to an outer surface or an inner surface of the one of the body-side wall and the distal-side wall such that the membrane layer covers the outlet, wherein the membrane layer is formed from a spunbond-meltblown-spunbond polypropylene (SMS PP) nonwoven, wherein the SMS PP nonwoven comprises a spunbond PP top layer, a meltblown PP middle layer, and a spunbond PP bottom layer and has a basis weight of about 40 gsm to about 80 gsm, wherein the filter assembly is configured to have an airflow rate at 0.18 psi of greater than about 10 cc/s and less than about 40 cc/s and a water hold-out of greater than about 0.9 psi and less than about 3.0 psi; and a multi-stage filter protection configured to protect the filter assembly, wherein the multi-stage filter protection comprises a prefilter and a protective panel covering the prefilter.

2. The ostomy pouch of claim 1, wherein the filter assembly is attached to an outer surface of one of the body-side wall and the distal-side wall, and the multi-stage protection is arranged inside the pouch.

3. The ostomy pouch of claim 1, wherein the filter assembly is attached to an outer surface of the distal-side wall and the prefilter and the protective panel are attached to an inner surface of the distal-side wall.

4. The ostomy pouch of claim 1, wherein the filter assembly, the prefilter, and the protective layer are attached to an inner surface of the distal-side wall.

5. The ostomy pouch of claim 1, wherein the protective panel is formed from a microperforated film, an embossed film, or a microperforated embossed film.

6. The ostomy pouch of claim 5, wherein the protective panel is formed from a microperforated film comprising a plurality of openings having a diameter of about 100 μm to 500 μm, wherein the plurality of openings are arranged to provide a pore-density of about 25 ppi to about 300 ppi, wherein the protective panel is sealed to the distal-side wall and/or the body-side wall along an outer peripheral seal.

7. The ostomy pouch of claim 5, wherein the protective panel is formed from a microperforated film comprising a first set of microperforations comprising a plurality of openings having a diameter of about 300 μm to about 500 μm, and a second set of microperforations comprising a plurality of openings having a diameter of about 50 μm to about 200 μm, wherein the first set of microperforations are arranged proximate a lower periphery of the protective panel and the second set of the microperforations are arranged above the first set of microperforations closer to the prefilter.

8. The ostomy pouch of claim 7, wherein the protective panel is sealed to the distal-side wall along a lower periphery to provide a horizontal seal, wherein at least a portion of the protective panel proximate the filter assembly is free of openings.

9. The ostomy pouch of claim 8, wherein the horizontal seal is a discontinuous heat seal or the protective panel includes at least one slit or opening proximate the lower periphery configured to allow liquid accumulated between the protective panel and the distal-side wall to flow down into the collection area.

10. The ostomy pouch of claim 1, wherein the prefilter includes a first layer formed from a reticulated foam or an open cell foam.

11. The ostomy pouch of claim 10, wherein the first layer is formed from a reticulated polyurethane (PU) foam.

12. The ostomy pouch of claim 10, wherein the prefilter further comprises a second layer, wherein the first layer is laminated to the second layer and the prefilter is attached to the distal-wall by heat sealing the second layer to an inner surface of the distal-wall.

13. The ostomy pouch of claim 12, wherein the second layer is formed from a polyester nonwoven or a spunbond-meltblown-spunbond polypropylene (SMS PP) nonwoven.

14. The ostomy pouch of claim 1, wherein the backing layer is formed from a low density polyethylene film.

15. The ostomy pouch of claim 1, wherein the filter media is formed from an activated carbon impregnated foam, wherein the activated carbon impregnated foam is hydrophobic.

16. The ostomy pouch of claim 15, wherein the filter media is formed from an activated carbon reticulated PU foam.

17. The ostomy pouch of claim 1, wherein the filter assembly is configured to provide a radial gas flow path through the filter media, wherein filter assembly is configured to direct the gas egressing through the outlet to flow through the membrane layer and radially flow through the filter media and exit the filter assembly through at least one gas outlet provided proximate an outer periphery of the filter assembly.

18. The ostomy pouch of claim 1, wherein the filter assembly and the multi-stage protection are configured and arranged to allow the gas collected in the collection area to flow through microperforations provided in the protective panel and flow through the prefilter and exit the ostomy pouch through the outlet and flow through the membrane layer and flow through the filter media radially before exiting the filter assembly.

* * * * *